(12) United States Patent
Schwabe

(10) Patent No.: US 6,582,700 B1
(45) Date of Patent: Jun. 24, 2003

(54) LINEAR ANTIGEN SUPPORTING UNITS

(75) Inventor: Christian Schwabe, Charleston, SC (US)

(73) Assignee: Medical University of South Carolina, Charleston, SC (US)

( * ) Notice: Subject to any disclaimer, the term of this patent is extended or adjusted under 35 U.S.C. 154(b) by 0 days.

(21) Appl. No.: 09/191,904

(22) Filed: Nov. 13, 1998

Related U.S. Application Data

(60) Provisional application No. 60/065,636, filed on Nov. 18, 1997.

(51) Int. Cl.$^7$ .................. A61K 39/00; G01N 33/531
(52) U.S. Cl. ............................. 424/185.1; 424/193.1; 424/194.1; 436/518; 436/543; 530/403; 536/123
(58) Field of Search .................. 424/193.1, 185.1, 424/194.1; 436/518, 543, 819; 530/403; 536/123

(56) References Cited

U.S. PATENT DOCUMENTS

| | | |
|---|---|---|
| 4,716,150 A | 12/1987 | Van Eldik et al. |
| 4,794,168 A | 12/1988 | Elder et al. |
| 5,229,490 A | 7/1993 | Tam |
| 5,580,563 A | 12/1996 | Tam |
| 6,217,873 B1 * | 4/2001 | Rose et al. ............... 424/193.1 |

FOREIGN PATENT DOCUMENTS

| WO | WO9303766 | 3/1993 |
|---|---|---|
| WO | 94/25071 | * 11/1994 |

OTHER PUBLICATIONS

James P. Tam, Synthetic Peptide Vaccine Design: Synthesis and Properties of a High Density Multiple Antigenic Peptide System, *Proc. Natl. Acad. Sci. USA*, 85:5409–5413 (Aug. 1988).

* cited by examiner

*Primary Examiner*—David Saunders
(74) *Attorney, Agent, or Firm*—Hana Verny; Theodore J. Leitereg

(57) ABSTRACT

The present invention concerns a synthetic construct comprising a linear core chain having two or more side chains pending directly from different points on the linear core chain. Each of the side chains comprises an epitopic site of an antigen or a peptide. The synthetic constructs are monomeric units that can be linked together or polymerized to form a polymer. In this embodiment the epitopic sites of the side chains may be the same or different. The linear core chain may be a linear sequence of amino acids having two or more of the same peptide pending directly from different points on the linear sequence. Another aspect of the present invention concerns a support having one or more of the above synthetic constructs or polymers coupled thereto. Another embodiment of the present invention is directed to antibodies raised against the above synthetic constructs or polymers. The antibodies can be purified using the above mentioned supports. Another aspect of the present invention is a vaccine comprising the above synthetic construct. The present invention also includes methods for synthesizing the above constructs and polymers.

17 Claims, 9 Drawing Sheets

21

22

23

24

25

26

27

28

29 30

31

32 33

34

LINEAR ANTIGEN SUPPORTING UNITS

CROSS-REFERENCE TO RELATED APPLICATIONS

This application claims the benefit of the subject matter disclosed in prior Provisional Patent Application Ser. No. 60/065,636, filed Nov. 18, 1997, the disclosure of which is incorporated herein by reference in its entirety.

BACKGROUND OF THE INVENTION

1. Field of the Invention

This invention relates to the production of novel synthetic peptide constructs and the use of such constructs as antigens in the production of antibodies, vaccines, antiviral agents, and the like. The antibodies produced in accordance with the invention may be used diagnostically or therapeutically. The constructs may also be used as vaccines.

Antibodies are important products of the immune system. An antibody is an immunoglobulin, which specifically binds to and is thereby defined as complementary with a particular spatial and polar organization of another molecule. The antibody can be monoclonal or polyclonal and can be prepared by techniques that are well known in the art. Antibodies may include a complete immunoglobulin or fragment thereof, which immunoglobulins include the various classes and isotypes, such as IgA, IgD, IgE, IgG1, IgG2a, IgG2b, and IgG3, IgM, etc. Fragments thereof may include Fab, Fv and F(ab')$_2$ Gab', and the like. In addition, aggregates, polymers, and conjugates of immunoglobulins or their fragments can be used where appropriate so long as binding affinity for a particular molecule is maintained.

Antiserum containing antibodies, usually referred to as polyclonal antibodies, is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, "Radioimmunoassay of Biologically Active Compounds," Prentice-Hall (Englewood Cliffs, N.J., U.S., 1976); Butler, *J. Immunol. Meth.* (1975) 7: 1–24; Broughton and Strong, *Clin. Chem.* 22: (1976) 726–732; and Playfair, et al., *Br. Med. Bull.* (1974) 30: 24–31.

Antibodies can also be obtained by somatic cell hybridization techniques, such antibodies being commonly referred to as monoclonal antibodies. Monoclonal antibodies may be produced according to the standard techniques of Köhler and Milstein, *Nature* (1975) 265:495–497. Reviews of monoclonal antibody techniques are found in "Lymphocyte Hybridomas," ed. Melchers, et al. Springer-Verlag (New York 1978), *Nature* (1977) 266:495; *Science* (1980) 208: 692, and *Methods of Enzymology* (1981) 73 (Part B):3–46. Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector which can be expressed in bacteria to produce recombinant proteins having the corresponding antibody binding sites.

Vaccines often comprise an antigen on a natural carrier such as a protein, a carbohydrate, a lipid or a liposome. Such vaccines are useful and have been employed for many years. There are, however, a number of art recognized problems with them. Several of these problems are related to the carrier. Since the carriers are isolated from natural sources, they are often not of uniform quality. Additionally, despite expensive and arduous purification efforts, it is difficult, and often impossible, to provide products completely free of natural contaminants. Such contaminants may themselves be antigenic. They cause the undesirable side reactions often associated with the use of vaccines, particularly fevers and tissue swelling. Additionally, the concentration of antigen may vary from one batch to another because the amounts of antigen, which react with the carrier or are absorbed on its surface are not uniform.

It is known that synthetic peptides can induce antibodies reactive with their cognate sequences in the native proteins. Specific antipeptide antibodies are useful laboratory reagents for confirming proteins from recombinant DNA, exploring biosynthetic pathways and precursors, and probing structural functions of proteins. Synthetic peptide antigens, conveniently available through chemical synthesis, can also be used for producing immunogens and for passive immunoprophylaxis.

One approach to preparing antipeptide antibodies is conjugation of a peptide to a known immunogenic carrier such as a protein. Examples of such carriers include albumins, serum proteins, e.g., globulins, ocular lens proteins and lipoproteins, bovine serum albumin, keyhole limpet hemocyanin ("KLH"), egg ovalbumin and bovine gamma-globulin. The peptide may also be linked to a synthetic polymer carrier or a liposome to give a macromolecular structure to the antigen carrier. Methods designed to avoid the use of carrier by polymerizing synthetic peptide antigens to give peptide polymers are also known. Although such materials are effective in producing animal antibodies, these materials are ambiguous in composition and structure. This shortcoming is particularly troublesome, for example, for antipeptide antibodies used for a human vaccine.

In an effort to address this problem, multiple antigen carrying structures were developed. Such structures are known and available commercially under the name Multiple Antigen Peptide System (MAPS). A small peptidyl core matrix is utilized bearing radially branching synthetic peptides as dendride arms. These molecules are produced by solid phase peptide synthesis beginning with three or four lysine residues which have only one kind of side chain-protecting group. Upon deprotection both amino groups are freed and a new similarly protected lysine derivative is condensed to the two free amino groups. This produces a branch chain with up to eight free amino groups which can then be used to synthesize directly onto the scaffolding the desired antigen which is usually a relatively short peptide.

These structures are typically subject to steric crowding, presenting disadvantages for synthesis, which suppress yields and lead to solutions of dendritic polymers with variable numbers of side chains. The practical limit for the MAPS approach is to include about 4 to 8 side chains, typically presenting the identical antigen. Moreover, the relatively tight steric crowding of side chains can interfere with antigen presentation.

2. Previous Disclosures

A synthetic peptide vaccine design and the synthesis and properties of a high-density multiple antigenic peptide system is described by Tam in *Proc. Natl. Acad. Sci. USA* (1988) 85:5409–5413.

A multiple antigen peptide system is disclosed in U.S. Pat. No. 5,229,490 issued Jul. 20, 1993 (Tam I).

A multiple antigen peptide system having adjuvant properties, vaccines prepared therefrom and methods of use therefor are discussed in U.S. Pat. No. 5,580,563 issued Dec. 3, 1996 (Tam II).

Synthetic peptides and use thereof in preparing calmodulin antisera are disclosed in U.S. Pat. No. 4,716,150 issued Dec. 29, 1987 (Van Eldik).

Multiple antigen peptides for use as HIV vaccines is discussed in PCT application WO 93/03766 published on Mar. 4, 1993 (Tam III).

A leukemia-associated virus immunogen, vaccine and assay are disclosed in U.S. Pat. No. 4,794,168 issued Dec. 27, 1988 (Elder).

SUMMARY OF THE INVENTION

One aspect of the invention concerns a synthetic construct comprising a linear core chain having two or more side chains preferably including an epitopic site pending directly from different points on the linear core chain. Each of the side chains comprises an epitopic site of an antigen.

Another aspect of invention is a polymer comprising one or more of the above synthetic constructs linked together. In this embodiment the epitopic sites of the side chains or respective constructs may be the same or different.

Another embodiment of the present invention is a synthetic construct comprising a linear sequence of amino acids having two or more peptides having the same sequence pending directly from different points on the linear sequence. The invention also includes a polymer comprising one or more of the above synthetic constructs linked together wherein the peptides or respective constructs may be the same or different.

Another aspect of the present invention concerns a support having one or more of the above synthetic constructs or polymers coupled thereto.

Another embodiment of the present invention is directed to antibodies raised against the above synthetic constructs or polymers by administering the above synthetic constructs or polymers to a host. The antibodies can also include antibodies that are purified using the above mentioned supports.

Another aspect of the present invention is a vaccine comprising the above synthetic construct.

Another aspect of the present invention is a method of synthesizing the present polymers. In the method a synthetic construct comprising a linear core chain having two or more side chains pending directly from different points on the linear core chain is formed. Each of the side chains comprises an epitopic site of an antigen. Two or more of the synthetic constructs are then coupled together. In one aspect of the method each of the side chains on the linear core chain comprises a first reactive functionality. The synthetic construct is prepared by combining this functionalized linear core chain with a peptide having a second functionality reactive with the first reactive functionality.

Another embodiment of the present invention is a synthetic construct comprising a linear sequence of amino acids, at least one of which is lysine and having a peptide pending from the terminal amino group. In this embodiment the peptide may be further linked to the terminal amino group of the lysine by an aspartic acid molecule.

In a particular embodiment of the present invention the epitopic site of the antigen is the active site of human relaxin. The invention also includes an antibody raised against the synthetic construct wherein the epitopic site of the antigen is the active site of human relaxin and in particular relaxin-H2.

DETAILED DESCRIPTION OF THE INVENTION

Definitions and Materials

Figure 1:
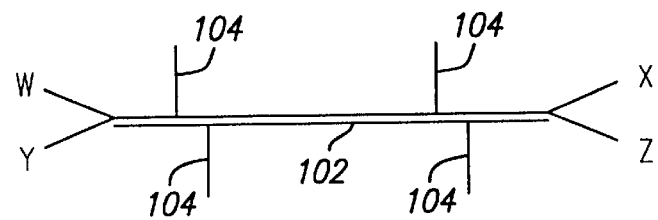
FIG. 1 is a schematic depiction of a synthetic construct in accordance with the subject invention.

Before proceeding with a detailed description of the present invention, a number of terms as used herein are defined.

Synthetic construct—a molecule produced synthetically or chemically as opposed to a naturally occurring or biologically derived molecule. The synthetic construct may be formed or synthesized from smaller molecules by procedures known in the art or it may be formed from a larger molecule, which may be naturally occurring or not, by degradation or other technique.

Linear core chain—in the context of the present invention the core chain from which the side chains are pending is linear as distinguished from dendritic or branched as in the case of the multiple antigen peptide system referred to above. Use of the term "linear" is not meant to imply any particular degree of rigidity as a requirement of the core chain. Accordingly, there is generally one side chain pending directly from a given point on the core chain (as distinguished from MAPS wherein more than one side chains pend from a point of the core chain, which is generally quite short, usually only one or two amino acids).

Side chain—a group that is pendant from the linear core chain. The side chain may comprise an epitopic site of an antigen or peptide.

Monomer—in the context of the present invention a monomer is a synthetic construct that is a unit of a polymer or from which a polymer is constructed. The monomers typically have functional groups for linking to one another. For example, a disulfide bond may be formed where each monomer has a thiol group; an amide bond may be formed where one monomer has a carboxyl group and another has an amino group; and so forth.

Polymer—a construct comprising at least two monomers, preferably, at least 2 monomers, usually about 2 to 4 monomers; however, in theory there is no limit on the number of monomers. The upper limit on the number of polymers is therefore governed by practical considerations.

Antigen—a molecule having sufficient molecular weight to elicit an immune response in an animal. For the most part, antigens have a molecular weight of at least about 2,500, preferably 5,000, more usually at least about 10,000 up to about 5,000,000, most usually from about 20,000 to 1,000,000. The antigen may be a poly(amino acid), i.e., polypeptide or protein, a polysaccharide, and combinations thereof. Such combinations include components of bacteria, viruses, chromosomes, genes, mitochondria, nuclei, cell membranes and the like. Antigens include cancer antigens such as PSA, CEA, AFP, CA19.9, etc., cardiac markers such as myoglobin, CKMB, etc., and so forth, microorganisms, e.g., viruses such as HIV virus, herpes virus (HSV) and the like, unicellular organisms, etc., blood proteins such as hemoglobin $A_1c$, HLA, and the like, surface membrane proteins, cytokines, interferons, hormones, growth factors, etc., immunoglobulins, fragments thereof, particularly monovalent fragments of immunoglobulins, e.g., Fab, Fv, etc., enzymes, naturally occurring receptors, e.g., T-cell receptors (including peptides and functional derivatives), hormone receptors, surface membrane receptors, lectins, etc.

Hapten—a compound capable of binding specifically to corresponding antibodies, but do not themselves act as immunogens (or antigens) for preparation of the antibodies. Antibodies, which recognize a hapten, can be prepared against compounds comprised of the hapten linked to an immunogenic (or antigenic) carrier. Haptens are a subset of ligands.

Epitopic site—a particular spatial and polar organization of a molecule that is recognized by a receptor.

Epitopic site of an antigen—that portion of an antigen that represents an epitopic site or immunodeterminant or antigenic determinant domain. Such portion is separate from the remaining portion of the antigen and is generally delineated by the area of interaction with a receptor, usually an antibody or another binding site such as an MHC-TCR complex. For example, for antigens that are proteins the epitopic site may be a low molecular weight peptide. The antigen may contain other epitopic sites. In the present invention the epitopic site of an antigen, as distinct from the entire antigen or other portions of the antigen, is coupled to the linear core chain through the side chain to form the present synthetic constructs.

As mentioned above, for protein antigens, the epitopic site is in the form of relatively low molecular weight as compared to the entire protein. For the most part the peptide will have about 8 to 40, usually 10 to 30, amino acids. The peptide may be prepared by synthesis from amino acids or by degradation of the antigen. The numbers of such peptides that are known are too numerous to list here. Some are commercially available and others may be prepared according to well-known synthetic procedures. The nature of the peptides and the procedures for forming them are well known in the art and will not be described in any detail hereinbelow. Some of the low molecular weight peptides that are of significance as epitopic sites are set forth in U.S. Pat. No. 5,229,490 at column 6, line 45, to column 8, line 8, the disclosure of which is incorporated herein by reference. Other such peptides are T cell receptor peptides discussed in U.S. Pat. No. 5,614,192. The present invention has application to any low molecular weight peptide antigen of interest.

Receptor—that part of a molecule capable of recognizing and binding to an epitope.

Ligand—a molecule having an epitope to which a receptor can bind; a receptor may be a ligand for another receptor. Examples of ligands by way of illustration and not limitation are agonists and antagonists for cell membrane receptors, toxins and venoms, viral epitopes, hormones (e.g., steroids, etc.) hormone receptors, peptides, enzymes, enzyme substrates, cofactors., lectins, sugars, oligonucleotides, nucleic acids, oligosaccharides, proteins, and monoclonal antibodies.

Complementary—refers to the topological compatibility or matching together of interacting surfaces of a ligand molecule and its receptor. Thus, the receptor and its ligand can be described as complementary, and furthermore the contact surface characteristics are complementary to each other.

Specific binding—the recognition by one of two different molecules for the other as compared to its having substantially less recognition of other molecules.

Specific binding molecule or cognate—one of two different molecules having an area on the surface or in a cavity that specifically binds to, and is thereby defined as, complementary with a particular spatial and polar organization of the other molecule. The members of a specific binding pair may be an antibody and antigen, antibody and hapten, ligand and receptor, and so forth.

Label or reporter molecule—a chemical entity capable of being detected by a suitable detection means, including, but not limited to, spectrophotometric, chemiluminescent, immunochemical, or radiochemical means. The reporter molecule can be conjugated to another molecule such as a ligand or an antibody by procedures well known in the art. Typically, the reporter molecule contains a functional group suitable for attachment to the ligand or antibody. The functional groups suitable for attaching the reporter group are usually activated esters or alkylating agents. Details of techniques for attaching reporter.groups are well known in the art. See, for example, Matthews, et al., *Anal. Biochem.* (1985) 151:205–209 and Engelhardt, et al., European Patent Application No. 0302175.

Reporter molecules are members of a signal producing system capable of being detected directly or through a specific binding reaction to produce a detectable signal. The reporter molecule can be isotopic or nonisotopic, usually nonisotopic, and can be a catalyst, dye, fluorescent molecule, chemiluminescent molecule, coenzyme, enzyme, substrate, radioactive group, certain particles such as carbon and the like.

As mentioned above, the reporter molecule is a member of a signal producing system, which may have one or more components, at least one of which is the reporter molecule. The signal producing system includes all of the reagents required to produce a measurable signal. Other components of the signal producing system can include substrates, coenzymes, enhancers, activators, chemiluminescent compounds, cofactors, inhibitors, scavengers, specific binding substances, and the like.

Support—a surface comprised of a porous or non-porous water insoluble material. Exemplary materials for use as a support include inorganic powders such as silica, magnesium sulfate, and alumina, natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass, ceramics, metals and the like. Natural or synthetic assemblies such as liposomes, phospholipid vesicles, and cells can also be employed. The surface can have any one of a.number of shapes, such as plate, well, strip, rod, particle, including bead and the like, and so forth. The surface may be a natural polymeric material or synthetic or modified naturally occurring polymer or glass.

The support may have any number of shapes such as particle including beads and the like. The support may be in the form of particles placed in a chromatography column or other container. Such columns can be used in known techniques for purifying antibodies such as, e.g., DEAE chromatography, ABx chromatography, and the like. The particles may also be used in the form of a bed and used in filtration of the antibodies, and so forth.

Binding of molecules to the support may be accomplished by well known techniques, commonly available in the literature. See, for example, "immobilized Enzymes," Ichiro Chibata, Halsted Press, New York (1978) and Cuatrecasas, J. Biol. Chem. (1970) 245:3059. The support is usually polyfunctional or capable of being polyfunctionalized or capable of binding a peptide through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like.

Protecting group—a group for blocking functional groups of an amino acid or other molecule for the purpose of preventing such group from reacting in a particular reaction in which the amino acid is a reactant. Such protecting group should have the property of being stable to the conditions for peptide linkage while being readily removable without destruction of a growing peptide chain. The protecting group is then removed when it is desired that the protected functional group should react. Such protecting groups, and the manner in which they are used, are well known in the art and have been described in detail in numerous patents and articles in the technical literature. See, for example, "Principles of Peptide Synthesis" (M. Bodanszky, Springer Verlag, Berlin, Heidelberg, New York, Tokyo (1984). Examples of such protecting groups, by way of example and not limitation, are t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentyl-ethoxycarbonyl, bromobenzyloxy, carbamyl, formyl, and the like. The particular protecting group chosen depends on the nature of the reaction to be performed and the conditions of such reaction such as temperature, pH, and so forth.

DETAILED DESCRIPTION AND PREFERRED EMBODIMENTS

The present invention provides for monomeric units, which are synthetic constructs that can be polymerized to form larger molecules. The polymers are useful as immunogens, vaccines and the like. The monomeric units are linear antigen supporting units in that the monomers comprise a linear core chain having two or more side chains preferably pending directly from different points on the linear core chain. Each of the side chains can present an epitopic site of an antigen. The monomeric units of the invention can present one or more of the same or different epitopic sites. The monomeric units allow for clean and uncrowded synthesis conditions for producing polymers that are more homogeneous than known dendritic polymers. Only one type of unit is synthesized and polymerized to produce a single antigen. The polymer is formed to the desired size by controlled addition of the. monomeric units. The invention also permits the production of several antibodies in one animal by employing as an immunogen a polymer comprising a plurality of coupled monomeric units that each has different epitopic sites.

One significant advantage of the present invention is that the linear monomers and polymers can be prepared with optimized spacing between the epitopic sites so that the epitopic sites are better presented in comparison to the MAPS molecules. The synthesis of the polymers is facilitated because there is little or no steric hindrance compared to the MAPS molecules. The size of the monomers and polymers can be adjusted after synthesis. Multiple epitopic sites can be incorporated into a single polymer by virtue of monomeric units each having a different epitopic site on its side chain(s). Antibodies prepared against the monomer can be readily separated by using one or more supports, each having multiple molecules of one of the monomeric units coupled thereto. The polymers in accordance with the present invention can be large enough to eliminate or reduce the need for adjuvants. Furthermore, the linear core chain of the present molecules is an unnatural one, which avoids the problem of using natural materials that may themselves be antigenic and cause the production of unwanted antibodies or other immune responses.

The present methods and molecules simplify the production of targeted antibodies to small known segments of the molecule and, together with the separation method one reaches nearly the specificity of a monoclonal antibody without the technical problems associated with monoclonal antibody production. The antibodies produced in accordance with the present invention have greater avidity typical of polyclonal antibodies. The avidity for antibodies produced in accordance with the present invention is usually about as good or better than observed for protein-conjugated ligands. The present methods and molecules provide for flexibility in that proteins may be attached to the side chains in lieu of specific peptides for the production of polyclonal antibodies without a need for adjuvants. Polymers may be constructed having a number of different epitopic sites of the same antigen. Antibodies produced in response to such a construct have superior avidity. Polyclonal antibodies having greater avidity can be prepared much more easily using the present constructs and polymers as immunogens, as compared with the time intensive procedures of the prior art for preparing polyclonal antibodies, in which multiple inoculations with different antigens are employed, are avoided by the instant approach. Additionally, the constructs and polymers of the present invention are useful for delivery of active therapeutics with or without the raising of antibodies thereto.

As mentioned above, one aspect of the present invention is a synthetic construct comprising a linear core chain having two or more side chains pending directly from different points on the linear core chain. Each of the side chains can present one or more epitopic sites. The linear core chain may be a chain of atoms other than hydrogen where the number of atoms is determined by counting along the shortest route of the chain. Typically, the number of atoms in the linear core chain is about 5 to 100, usually 20 to 60 atoms, each independently selected from the group consisting of carbon, oxygen, nitrogen, sulfur and sometimes phosphorous. As a general rule, the length of a particular linear core chain can be selected to provide for convenience of synthesis and sufficient spacing between the pending side chains to provide for optimum antigen presentation for recognition by its cognate (as can readily be determined using standard techniques and criteria). The predominant atom in the chain is carbon where the valency of carbon is satisfied by hydrogen or by an atom such as oxygen, carbon, nitrogen and sulfur. Oxygen will normally be present as oxo or oxy, bonded to carbon, sulfur, nitrogen or phosphorous; nitrogen will normally be present as amino, normally bonded to carbon; sulfur is analogous to oxygen except that sulfur may be in the form of thiol when present at a terminal position on the chain.

The linear core chain is generally synthesized from smaller molecules that have functional groups that provide for linking of the molecules in a linear chain. Such functional groups include carboxylic acids, amines, and hydroxy- or thiol-groups. In accordance with the present invention the linear core chain may have one or more side groups pending from the core chain. The side groups have a functionality to provide for linking of the epitopic site of the antigen to the core chain to form the side chains.

Common functionalities resulting from the reaction of the functional groups employed are exemplified by forming a covalent bond between the linking group and the molecule to be conjugated. Such functionalities are disulfide, amide, thioamide, dithiol, ether, urea, thiourea, guanidine, azo, thioether, carboxylate and esters and amides containing sulfur and phosphorus such as, e.g. sulfonate, phosphate esters, sulfonamides, thioesters, etc., and the like.

In a preferred embodiment of the present invention, the linear core chain is conveniently composed primarily of amino acids but also may include thioacids and other carboxylic acids having from one to five carbon atoms. The linear core chain may have from 3 to 30, preferably 5 to 20, amino acids per synthetic construct and 1 to 3 thioacids or other carboxylic acid. Any amino acid may be employed. Preferably, the linear core chain is composed of amino acids selected from the group consisting of lysine, cysteine, aspartic acid, gamma-aminobutyric acid, glycine, alanine and longer chain omega amino acids. The thioacids include thioacetic acid, thiopropionic acid, thiobutyric acid, and so forth. The amino acids are linked together to form the linear core chain in such a way as to provide for certain side groups with a functional group for linking to an epitopic site of an antigen.

The use of lysine and other naturally occurring amino and other carboxylic acids is advantageous where the present invention is applied to the production of a vaccine. Such naturally materials may be processed by the animal to which the vaccine is administered following the usual metabolic pathways. However, amino acids and other carboxylic acids that are not naturally occurring may be employed. The acids may be in either the D or L form or racemic mixtures thereof.

Figure 2:
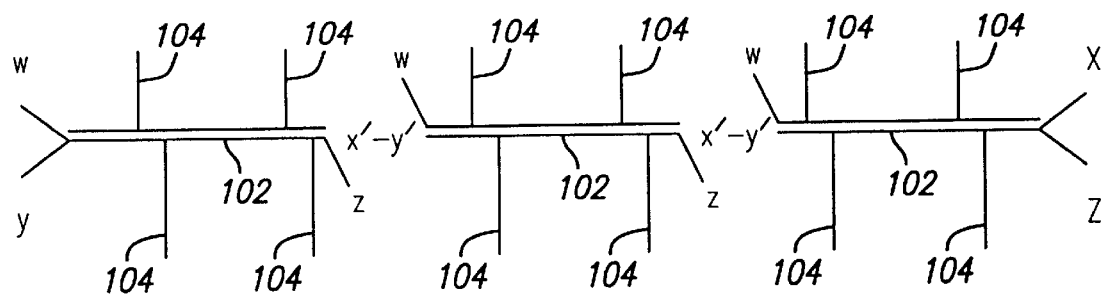
FIG. 2 is a schematic depiction of a polymer in accordance with the subject invention.

In one embodiment, the monomer and polymer constructs of the present invention are represented in schematic form as seen in FIGS. 1 and 2, respectively. Referring to FIG. 1, monomer 100 is depicted having a linear core chain 102 with side chains 104 pending therefrom. Functional group X and functional group Y are related in that they are capable of reacting with one another to form a covalent bond and thereby link two or more monomers to form a polymer 120 as depicted in FIG. 2. The functional groups may be selected from those described above, e.g., in conjunction with the definition of monomer. The monomers may be the same or different. When the monomers are different, the differences can reside in the composition of linear core chain 102 or side chains 104, or both. Furthermore, for each monomer, side chains 104 may be the same or different. Monomer 100 may also comprise W and Z, which may be another functional group such as carboxyl, amino, sulfhydryl, and the like. Polymer 120 can be formed by the reaction of X and Y with each other, the bound groups being shown as X'-Y', as in FIG. 2.

One particular embodiment of the present invention is a situation wherein X on one monomer is capable of reacting with X on another monomer to form a dimer, trimer, and so forth. Such a situation is achieved, for example, where X is a thiol, which reacts with another thiol to form a disulfide linkage. A particular example of such a linear core chain is shown hereinbelow.

Formula I is one embodiment of a monomer in accordance with the present invention and is presented by way of illustration and not limitation:

$$R^2S\text{—}(CH_2)_n\text{—}CH(Z)\text{—}C(O) \qquad \text{Formula I}$$

wherein:

Z is H, NH$_2$, or protected or blocked NH$_2$ and

R$^2$ is Acm, Trt or H and n is 0 to 5.

Formula II is another embodiment of a monomer in accordance with the present invention and is presented by way of illustration and not limitation:

Formula II

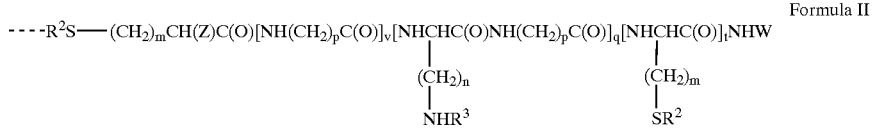

wherein:

Z is H, C(O)OH or NH$_2$ or protected or blocked NH$_2$;

R$^2$ is independently selected from the group consisting of H, a protecting group, benzyl or pyridyl;

t is 0 or 1;

W is C(O)R$^1$ wherein R$^1$ is OH, NH(CH$_2$)$_p$C(O)OH or (CH$_2$)$_p$—COOH, when t is 1 and W is H when t is 0;

R$^3$ is H or an antigen;

m, n and p are independently 1 to 5, v is 0 to 1, and q is 1 to 4.

In a preferred embodiment, m is 1 to 2, n is 3 to 4, p is 2 to 3 and q is 2 or 4; more preferably, m is 1, n is 4, p is 3 and q is 2 or 4; t and v are independently 0 or 1 with the proviso that, when t is 0, v is 0. When m is 1, the moiety containing m is a thiopropionic acid derivative. When n is 4, the moiety containing n is a lysine derivative. When p is 3, the moiety containing p is a gamma-aminobutyric acid derivative. When t is 1, the moiety defined by t is a cysteine derivative.

In the above embodiment, lysine with two amino groups is joined in a peptide bond through its carboxyl group and through its alpha-amino group to other members of the linear core chain. As a result, the terminal amino group of lysine, and the butylene chain to which it is attached to the alpha-carbon atom of lysine, is pendant from the linear core chain. This terminal amino group is available as a functional group to which an epitopic site of an antigen is attached to form the synthetic constructs of the invention. The gamma-aminobutyric acid is joined through its gamma-amino group in a peptide bond to the carboxyl group of lysine and further through its carboxyl group to the other members in the linear core chain. In this embodiment, the basic element of the linear core chain of the monomer is the lysine-gamma-butyric acid dipeptide unit. The moiety providing the thiol group is 3-thioproprionic acid linked through its carboxyl group to the linear core chain. Other moieties may be linked together to form the linear core chain as desired through appropriate peptide linkages. The linear core chain or a side group pending therefrom usually contains one or more free functional groups other than those involved in linking epitopic sites of an antigen to the construct. Such free functional groups may be used to bind the construct to a resin either during its synthesis or during further reactions of the construct.

The chemistry for performing the types of syntheses to form the linear core chain as a peptide chain is well-known in the art. See, for example, Marglin, et al., *Ann. Rev. Biochem.* (1970) 39:841–866. In general, such syntheses involve blocking, with an appropriate protecting group, those functional groups that are not to be involved in the reaction. The free functional groups are then reacted to form the desired linkages. Both the synthetic constructs and the polymers can be produced on a resin as in the Merrifield synthesis (Merrifield, *J. Am. Chem. Soc.* (1980) 85:2149–2154 and Houghten et al., *Int. J. Pep. Prot. Res.* (1980) 16:311–320. The monomer or the polymer is then removed from the resin according to known techniques.

An excellent summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p 46., Academic Press (New York), for solid phase peptide synthesis and E. Schroder, et al., "The Peptides, vol. 1, Academic Press (New York), 1965 for solution synthesis.

In general, these methods comprise the sequential addition of one or more amino acids, or suitably protected amino acids, to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. Alter all the desired amino acids have been linked in the proper sequence, any remaining protecting groups (and any solid support) are removed sequentially or concurrently, to afford the final peptide.

A preferred method of preparing the synthetic constructs of the present invention involves solid phase peptide synthesis. The carboxyl group of an amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are Wang resin (p-benzyloxybenzyl alcohol) chloromethylpolystyrene, divinylbenzene polymer, hydroxy-methyl-polystyrene divinylbenzene polymer, and the like. See, for example, P. Rivaille, et al., *Hely. Chim. Acta.* (1971) 54, 2772. After the synthesis is complete the synthetic construct is removed from the resin by conventional means such as ammonolysis, acidolysis and the like. Any protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like. The fully deprotected peptide construct may then be purified by techniques known in the art such as chromatography, for example, adsorption chromatography; ion exchange chromatography, partition chromatography, high performance liquid chromatography, thin layer chromatography, and so forth.

The selected peptide representing an epitopic site of an antigen may be separately synthesized or otherwise obtained and joined to the side group pending from the linear core chain on the resin or after removal of the linear core chain from the resin. Alternatively, the selected peptide representing the epitopic site of the antigen may be synthesized on the construct while on the resin. In any of the above approaches, the linking of the epitopic site to the side group of the linear core chain may be carried out using one or more of the techniques described above for the synthesis of peptides.

A particular embodiment of the present invention and process for its preparation is depicted in Scheme A shown in FIG. 7A–FIG. 7D. The linear core chain with the pendant side groups is prepared synthetically using procedures such as those described above for peptide synthesis. As can be seen, the basic components of the construct are gamma-aminobutyric acid and lysine. The linear core chain is prepared by first reacting gamma-aminobutyric acid with lysine and, in alternating fashion, reacting the resulting product with gamma-butyric acid and lysine until the desired number of molecules of each is obtained in the linear core chain product. The alternate reactions occur by an amino group of one product reacting with a carboxyl group of the molecule to be added to the growing linear core. Where a resin is employed, the final product is released from the resin either as an amide or an ester depending on the linker chosen.

In the final product, at one end of the linear core chain is a cysteine wherein the thiol of the cysteine has a protecting group (Acm) and the amino group thereof is acetylated. The terminal amino groups of the lysines are linked to aspartic acid by means of an amide linkage with the carboxyl group of aspartic acid adjacent the amino group. The amino group on the aspartic acid moiety provides the functional group for linking to the epitopic site of an antigen (represented by —C(Q)-Antigen-$NH_2$ in the above formula).

In the preparation of the linear core chain as represented in Scheme A, the following reactions are carried out wherein the R groups are defined as: R3 is an amino protecting group, e.g., tert-butoxycarbonyl; $R^4$ is a carboxyl activating group, e.g., N-hydroxybenzotriazole ester; $R^5$ is an amino protecting group different from $R^3$, e.g., 9-fluorenylmetoxycarbonyl; $R^6$ is a carboxyl protecting group that is the same as or different than $R^8$; $R^8$ is a carboxyl protecting group linked to a solid support such as p-methylbenzhydroxylamine resin.

Referring to Scheme A, gamma-aminobutyric acid (GABA) is treated according to conventional procedures to prepare compound 10 wherein the amine function is protected with $R^3$ and the carboxyl is protected with $R^8$. 10 is treated by known procedures to remove $R^3$ and give compound 11, which is reacted with compound 12, a lysine molecule having amino protecting groups $R^3$ and $R^5$ and carboxyl activating group $R^4$. The resulting product 13 results from the formation of an amide linkage between the activated carboxyl group of 12 and the free primary amine group of compound 11. Removal of $R^3$ from 13 results in compound 14, which is reacted with compound 15, GABA having its amino group protected with $R^3$ and its carboxyl group activated with $R^4$, to give compound 16. The amino protecting group $R^3$ is removed from 16 to give 17, which is reacted with 12 to give compound 18. The latter compound is treated to remove its $R^3$ protecting group to give compound 19, which is reacted with compound 15 to give compound 20. The reactions continue in a similar fashion to ultimately produce compound 28 (which may also be represented as $R^3[NHGABA\text{-lysine}(NHR^5)]_4GABA\text{-}OR^8$. Thus, as can be seen, compound 28 has a linear core chain with four repeating units of NHGABA-lysine(NHR$^5$) wherein the NH group of the terminal GABA molecule is protected with $R^3$ and the terminal carboxyl of the lysine is linked through an amide linkage to amine group of a GABA molecule. Compound 30, namely, cysteine with its amino group acetylated and its thiol group protected with Acm, is reacted with 29, which is compound 28 with the $R^3$ protecting group removed, to give 31. Removal of protecting groups $R^5$ from the lysines of compound 31 yields 32. Compound 33, which is aspartic acid having an $R^4$ activated carboxyl group, an $R^6$ protected carboxyl group and an $R^5$ protected amine group, is reacted with 32 to give compound 34.

Compound 34 may also be written as follows:

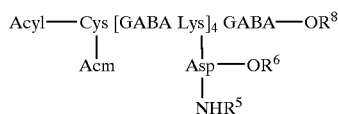

wherein Acyl=acetyl group, Cys=cysteine, GABA is defined above, Lys=lysine, Acm is defined above.

Compound 34 may also be written as follows:

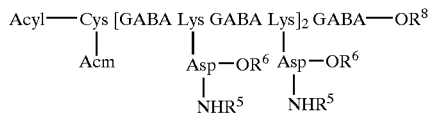

Compound 34 is treated to remove the protecting group $R^5$ to give compound 35, which is reacted with antigen having an activated carboxyl group to give synthetic construct 36. Activation of the carboxyl group of the antigen is carried out according to conventional procedures well known in the art and discussed above. As mentioned above, the peptide may be released from the solid support either as an amide or an ester depending on the linker chosen. In the situation depicted, the resin is p-methylbenzhydroxylamine and compound 36 is released from the support as an amide.

Compound 36 may also be written as follows:

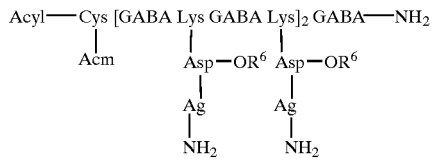

wherein Acyl=acetyl group, Cys=cysteine, GABA is defined above, Lys=lysine, Acm is defined above, Ag=antigen.

The above reaction scheme demonstrates one synthetic approach to preparation of the linear constructs of the present invention. The invention has tremendous versatility with respect to the choice of starting materials and synthetic pathways for the preparation of the present constructs and polymers. One merely must keep in mind the basic premise of the invention, namely, a linear core chain having pending side chains to which are attached epitopic sites of antigens. As can be seen from above, lysine, GABA, aspartic acid and cysteine are one set of molecules that may be conveniently utilized to form the present constructs. Many other approaches will be suggested to the skilled artisan in view of the disclosure herein.

Figure 8A:
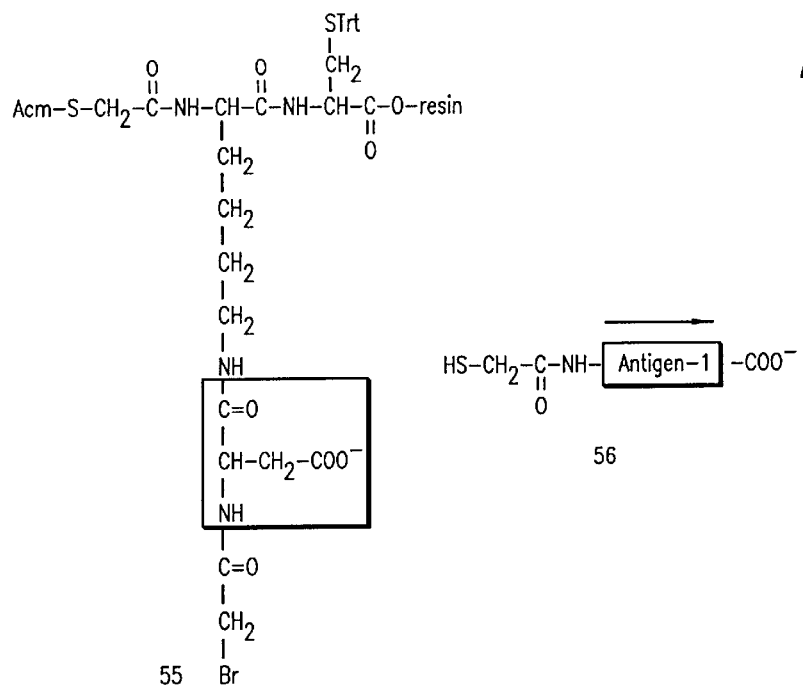
FIG. 8A is a schematic depiction of a portion of Scheme B for the preparation of another embodiment of the present invention.
Figure 8A:
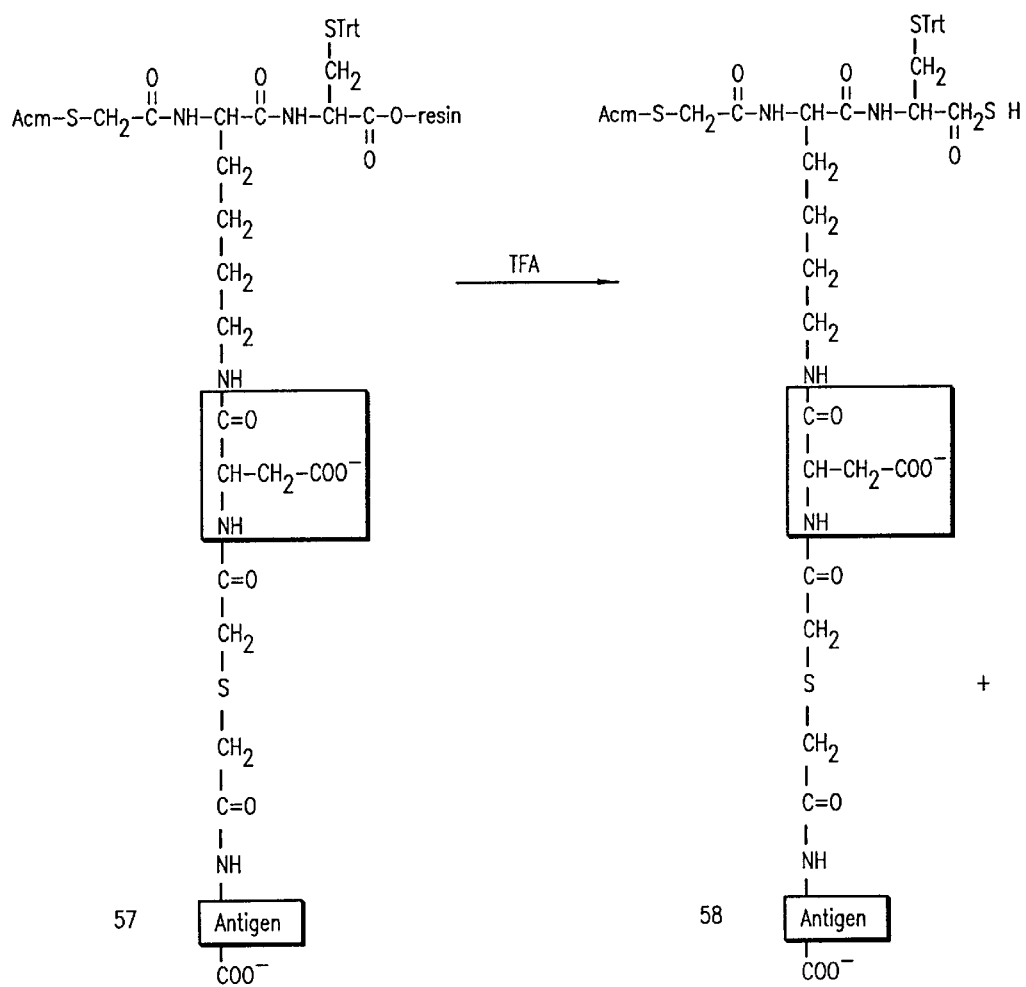
Figure 8B:
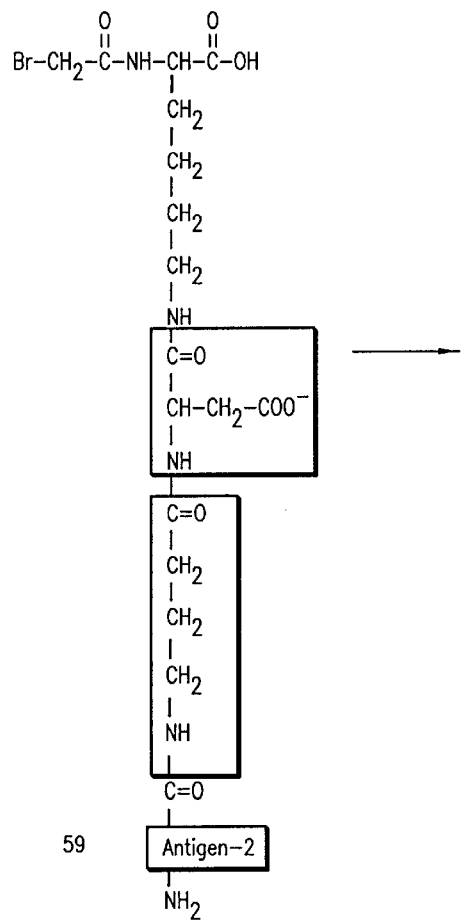
FIG. 8B is a schematic depiction of another portion of Scheme B for the preparation of another embodiment of the present invention.
Figure 8B:
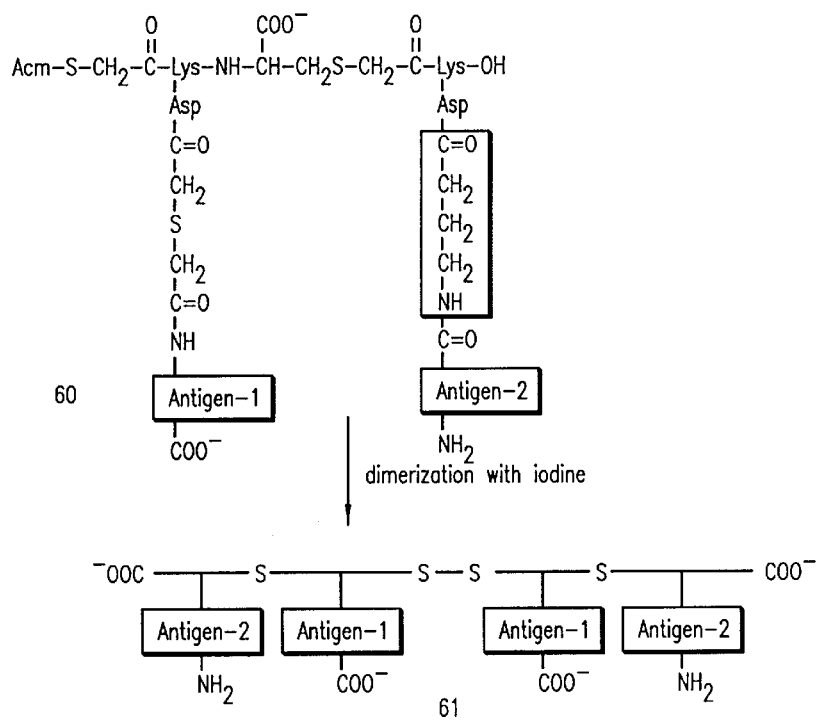

Another approach to the preparation of a synthetic construct in accordance with the present invention is set forth in Scheme B depicted in FIG. 8A–FIG. 8B, illustrating preparation of a monomer having two different antigens. The precursor compounds and the reactions to produce the synthetic constructs are similar to those described above for the preparation of construct 36. In the approach in Scheme B, the synthesis is conducted on a resin. The cysteine is bound to a resin by means of its carboxyl group. The thiol group of the cysteine is protected with a trityl-protecting group (Trt). Lysine is reacted with thioacetic acid having its thiol group protected with Acm. The bond is formed between the carboxyl group of the thioacetic acid and the alpha-amino group of the lysine. The resulting product is attached to the resin by virtue of the formation of a peptide bond between the carboxyl group of the product and the amino group of the cysteine on the resin. A peptide bond is formed between the carboxyl group adjacent the amino group of aspartic acid and the terminal amino group of lysine.

As shown in Scheme B, bromoacetic acid is reacted with the free amino group of aspartic acid to give compound 55. Compound 57 is obtained from 55 by reaction, under nucleophilic displacement conditions, between the thiol group of compound 56 and the carbon atom of 55 bearing the bromine atom. Compound 56 is the reaction product of compound 55 and compound 12. The trityl-protecting group is removed from 57 by protonation using trifluoroacetic acid (TFA) to give 58 free of the resin. Compound 59 is formed from its precursor molecules in a manner similar to that described above. The precursor molecules for 59 are lysine, bromoacetic acid, aspartic acid, GABA and antigen-2. Compounds 58 and 59 are linked together by reaction of the thiol sulfur of 58 and the carbon atom of 59 bearing the bromide to yield compound 60, which is treated to remove the protecting group Acm. Compound 61 is formed by dimerization of 60 to form a disulfide bond.

Figure 9:
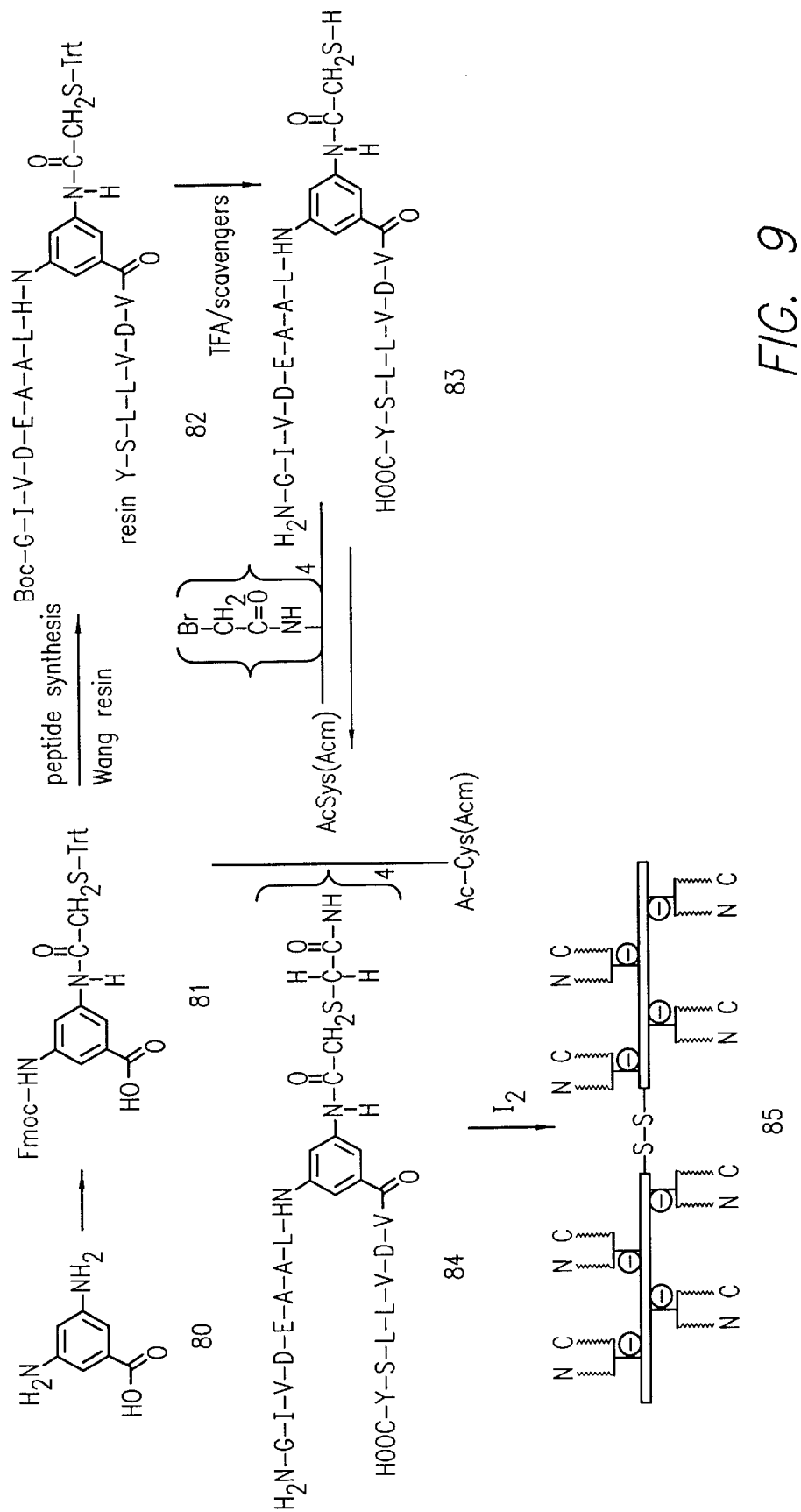
FIG. 9 is a schematic depiction of another embodiment of the present invention and process for its preparation.

Another approach to the production of the constructs of the present invention is set forth in Scheme C depicted in FIG. 9. 3,5-diaminobenzoic acid 80 is treated to protect one of its amino groups with protecting group Fmoc, which is then reacted with thioacetic acid having its thiol group protected with a Trt protecting group to give compound 81, having an amide linkage joining 80 with the thioacetic acid. Peptide synthesis is carried out on a solid support (Wang resin) according to conventional techniques. The resulting product 82 has antigen G-I-V-D-E-A-A-L linked to the free amino group of 81 and antigen Y-S-L-L-V-D-V linked to the carboxyl group of 81. The Trt and Boc protecting groups are removed by hydrolysis with TFA in the presence of scavengers, which are for the purpose of preventing side reactions of the released protecting moiety. Such scavengers are well known in the art and include, for example, anisole, thiocresol, and so forth. The resulting product 83 is linked to a linear core chain construct similar to compound 32 depicted in Scheme A (where the terminal amino group of the lysines have been bromoacetylated) above to give compound 84. Dimerization of 84 in the presence of iodine gives polymer 85.

It is noteworthy in the above embodiment that each of the pending side chains has two epitopic sites, each of the two being from different antigens. However, this embodiment is distinguished from that in the known MAPS approach. The side chains in the above embodiment each depend from the linear core chain whereas with MAPS the chain is branched from a core molecule. Thus, although the present invention contemplates more than one epitopic site at the end of one or more of its side chains, there is still a linear core chain from which the side chains depend.

Figure 3:
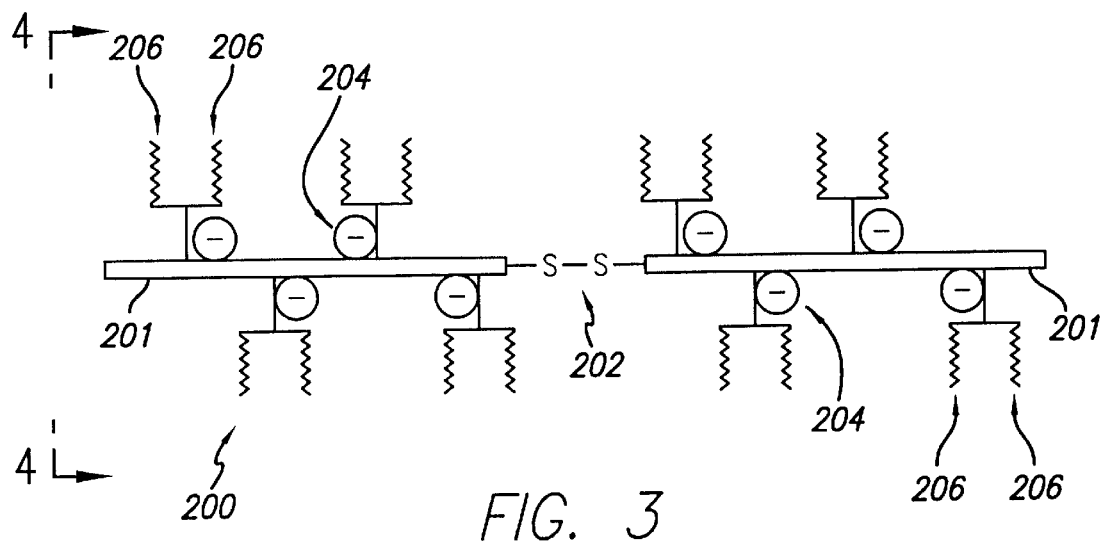
FIG. 3 is a schematic depiction of a particular embodiment of a polymer in accordance with the subject invention.
Figure 4:
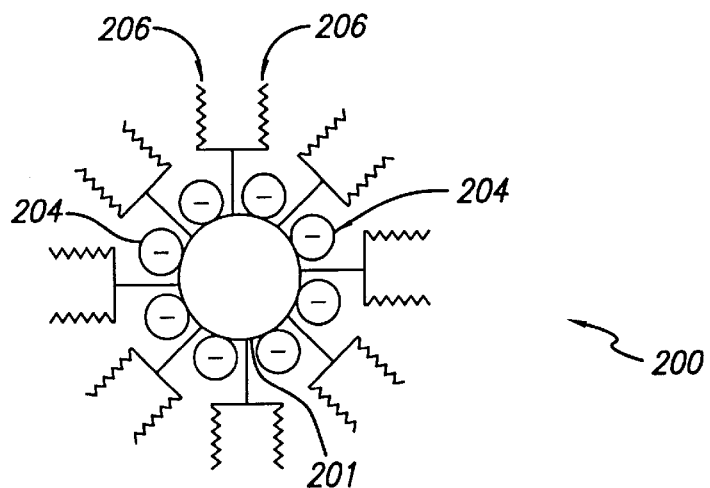
FIG. 4 is a schematic depiction of the polymer of FIG. 3 viewed in the direction of line 4—4.

A particularly attractive feature of the present invention may be explained with reference to FIGS. 3 and 4, wherein compound 85 is depicted schematically, as having a linear core chain 200 composed of two monomers 201 with disulfide bond 202 linking the monomer units. Negative charges 204 are a representation of the overall net charge of the molecule near the juncture of the pending side chains 206 and the linear core chain. This net charge is the result of the presence of an aspartic acid moiety in each of the side chains. As mentioned above, one significant advantage of the present invention is that the linear monomers and polymers can be prepared with sufficient spacing between the epitopic sites so that the epitopic sites are better presented in comparison to the MAPS molecules. This feature is explained with reference to FIG. 4. As can be seen, the antigen molecules on polymer 85 are disposed in such a manner as to maximize the distance between them. This results because of the repulsive forces of the negative charges introduced by the presence of the aspartic acid moieties. The result achieved with polymer 85 is a "bottle brush" configuration where each of the epitopic sites seek maximum distance from the others, thereby optimizing the presentation of the epitopic sites to, for example, an antibody. Accordingly, the present invention provides an elegant system for tailoring the synthetic constructs and polymers produced thereby. By selection of appropriate components of the side chains one can achieve repulsive or attractive forces depending on the desired disposition of the epitopic sites of the antigens in the products of the invention.

Figure 5:
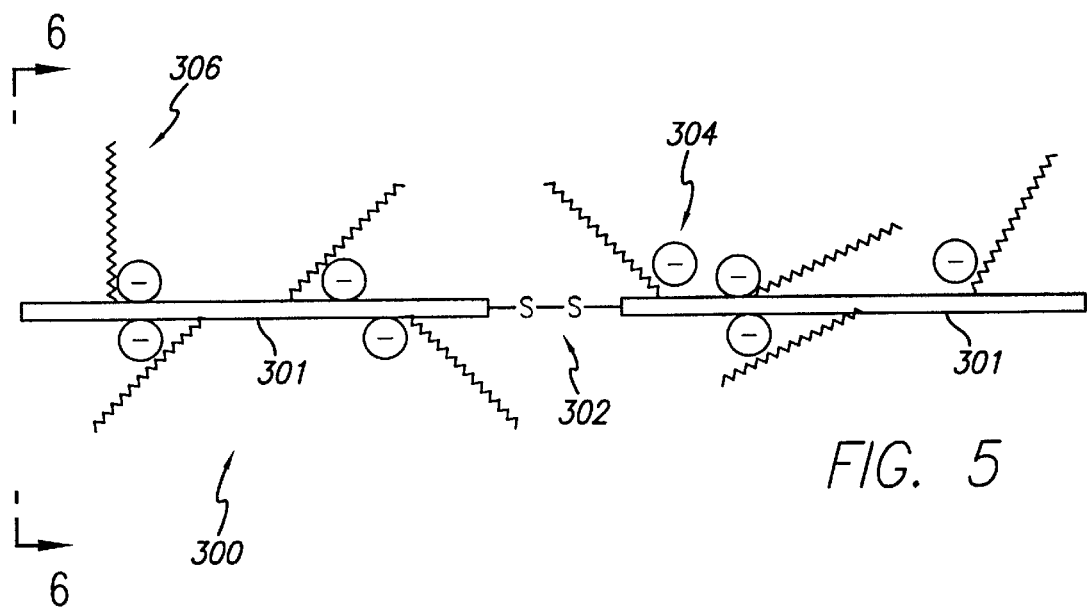
FIG. 5 is a schematic depiction of a particular embodiment of a polymer in accordance with the subject invention.
Figure 6:
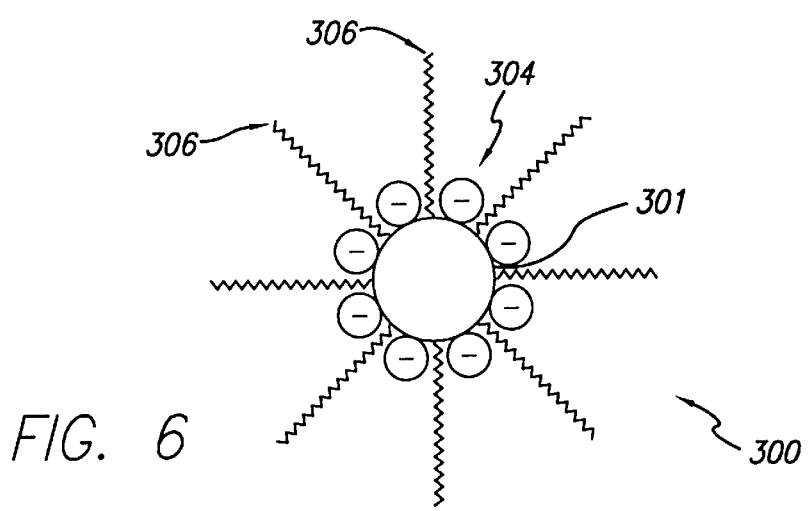
FIG. 6 is a schematic depiction of the polymer of FIG. 5 viewed in the direction of line 6—6.
Figure 7A:
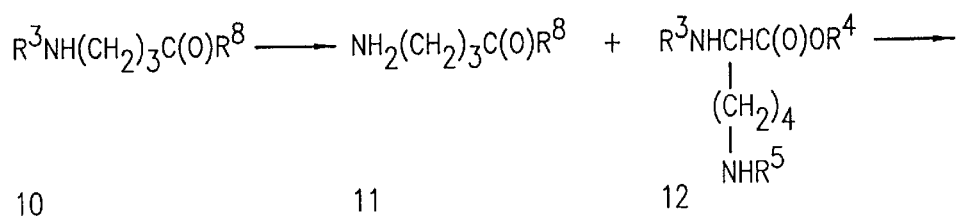
FIG. 7A is a schematic depiction of a portion of Scheme A for the preparation of one embodiment of the present invention.
Figure 7A:
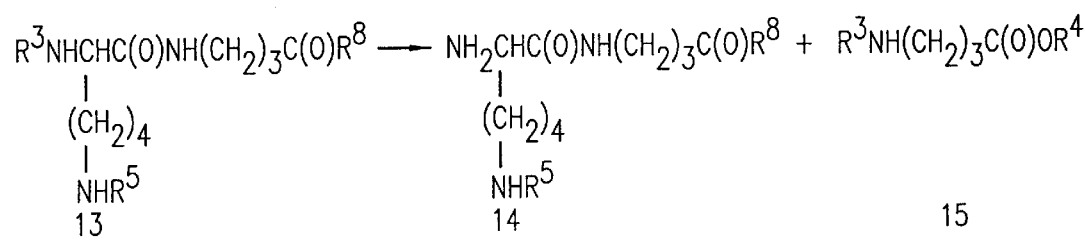
Figure 7A:
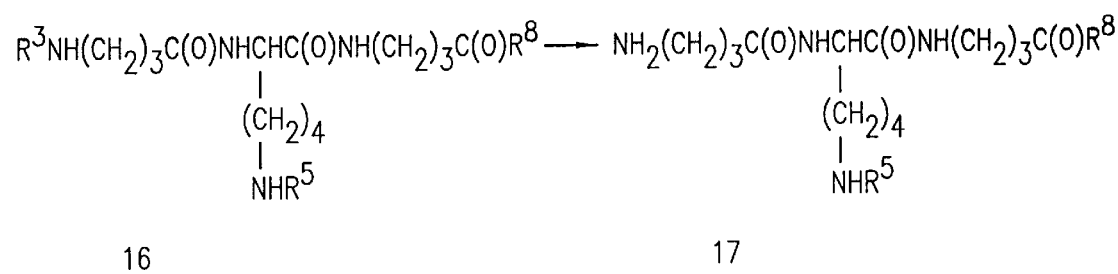
Figure 7A:
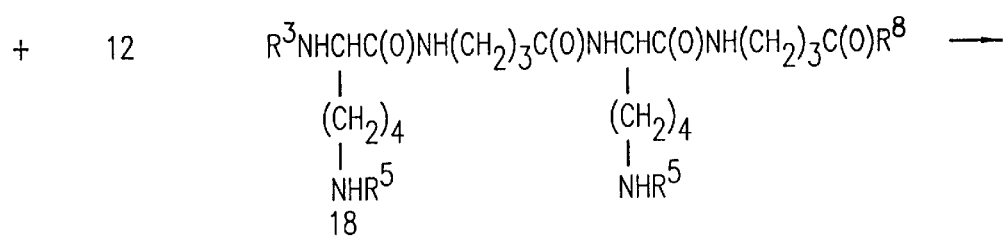
Figure 7A:
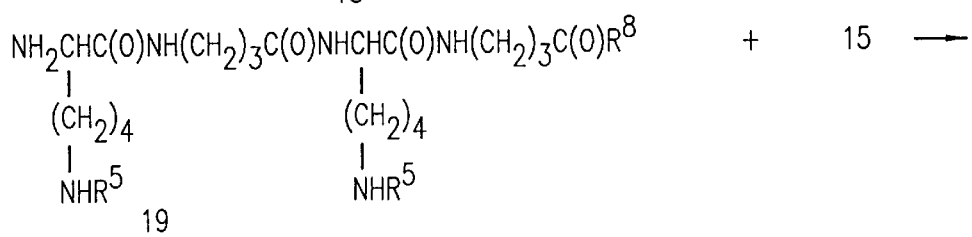
Figure 7A:
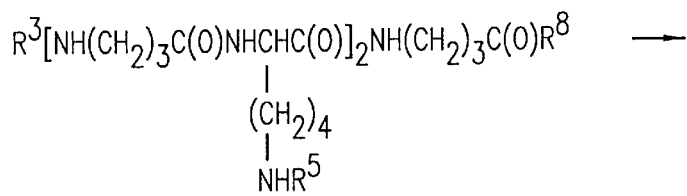
Figure 7B:
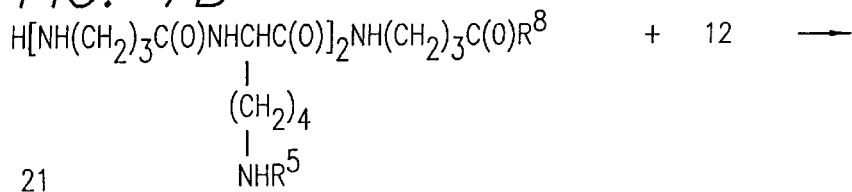
FIG. 7B is a schematic depiction of another portion of Scheme A for the preparation of one embodiment of the present invention.
Figure 7B:
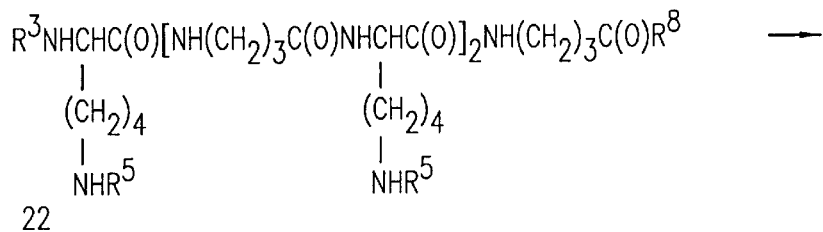
Figure 7B:
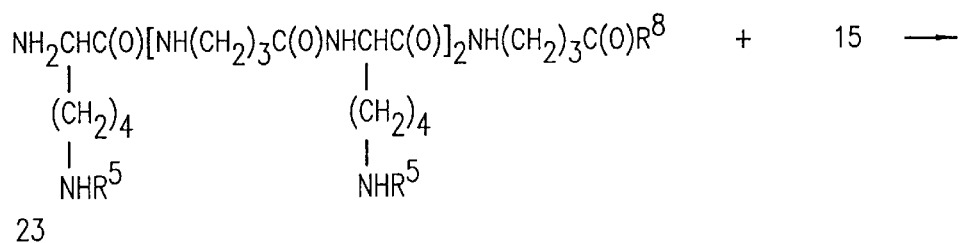
Figure 7B:
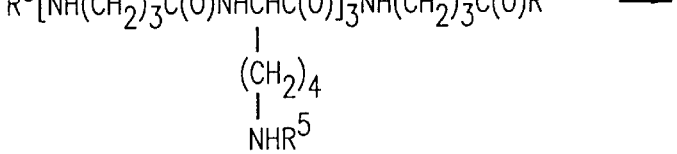
Figure 7B:
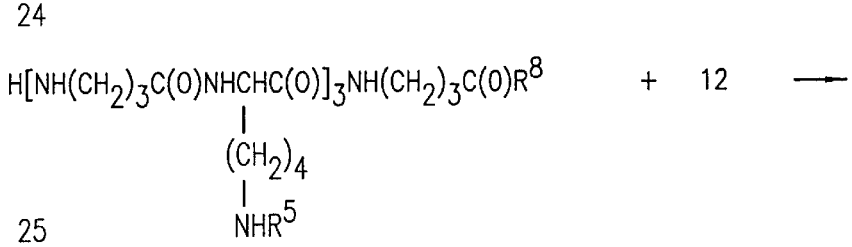
Figure 7B:
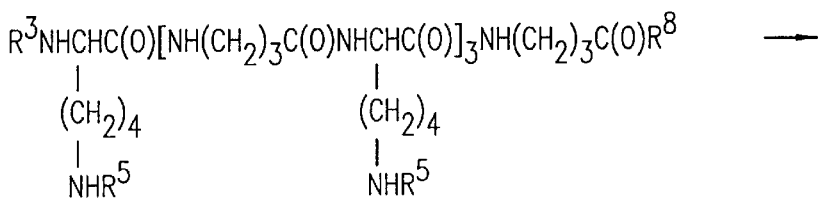
Figure 7B:
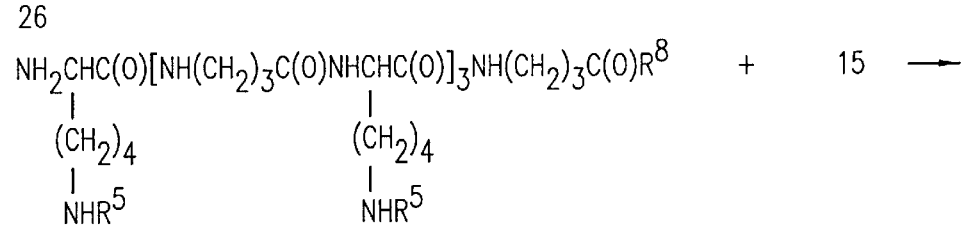
Figure 7C:
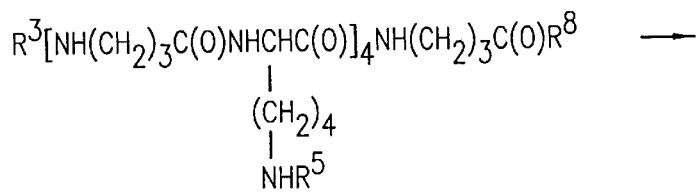
FIG. 7C is a schematic depiction of another portion of Scheme A for the preparation of one embodiment of the present invention.
Figure 7C:
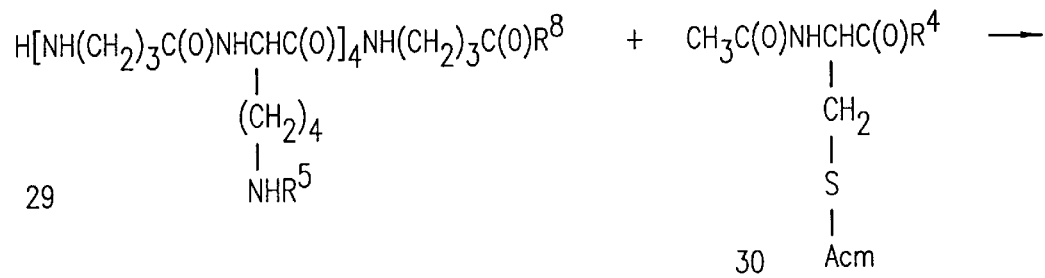
Figure 7C:
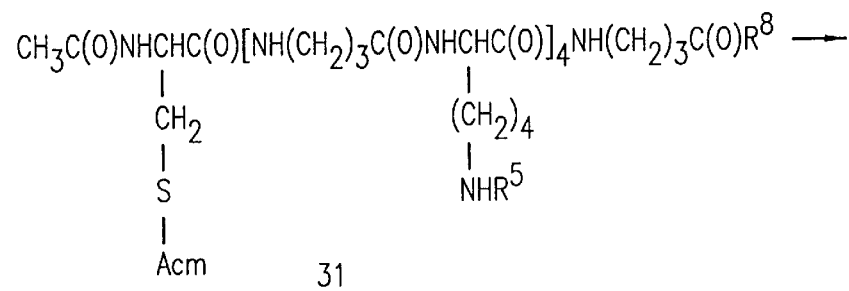
Figure 7C:
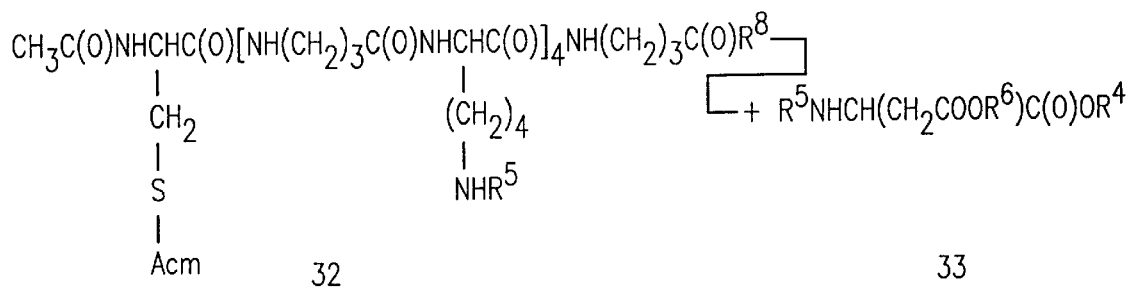
Figure 7C:
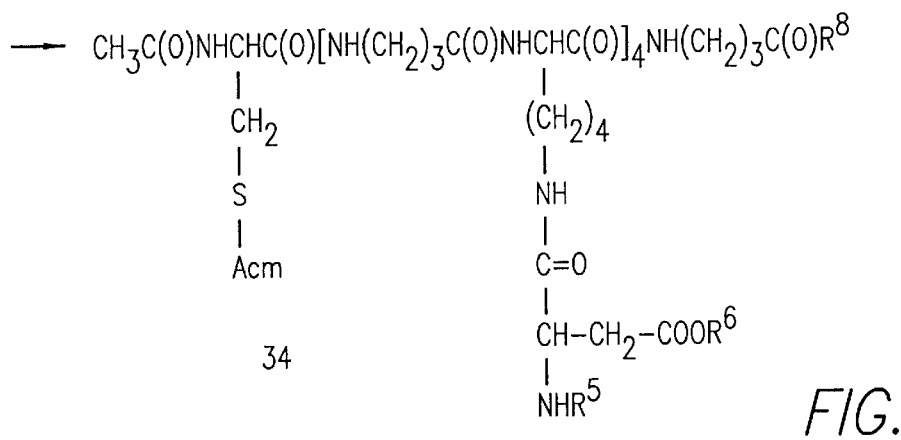
Figure 7D:
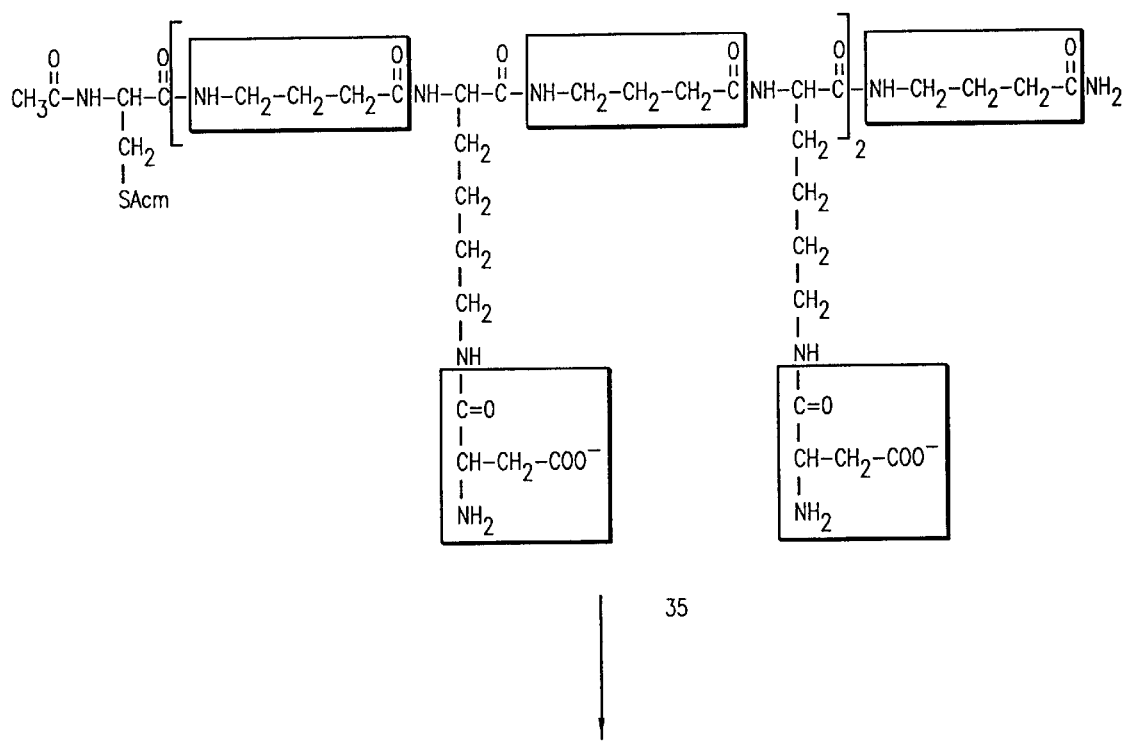
FIG. 7D is a schematic depiction of another portion of Scheme A for the preparation of one embodiment of the present invention.
Figure 7D:
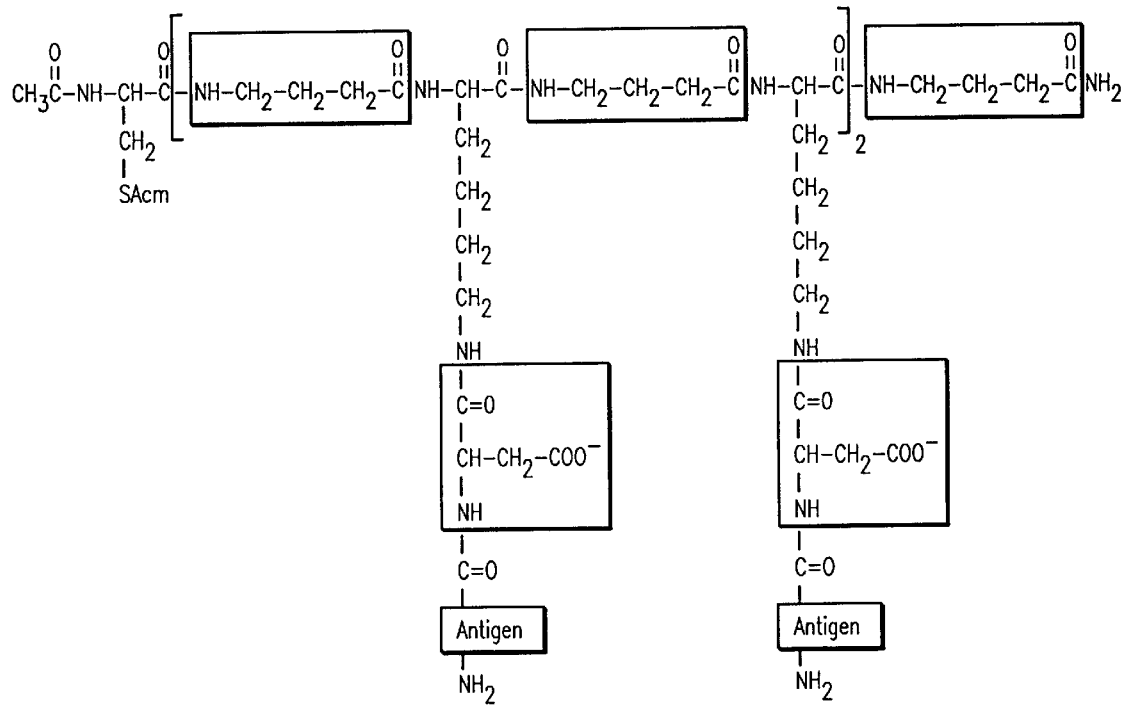

FIGS. 5 and 6 depict another embodiment of the present invention where only one epitopic site of a single antigen is attached to each pending side chain. Referring to FIG. 5, polymer 300 is comprised of two monomers 301 joined by disulfide linkage 302. Negative charges 304 are a representation of the overall net charge of the molecule near the junction of the pending side chains 306 and the core chain. Referring to FIGS. 5 and 6, epitopic sites are depicted in somewhat three dimensional form where 306a is approximately at 12 o'clock, 306b is at approximately 1 o'clock, 306c is at approximately 4 o'clock, 306d is at approximately 6 o'clock, and so forth. The two monomers are the same and can twist about the S—S bond. The conformation is close to linear because of repulsive forces.

The products of this invention can be employed to produce vaccines using any of the procedures known to those skilled in the art. Vaccine preparation techniques are generally known in the art as described by Duffy (ed.) in Vaccine Preparation Techniques, published by Noyes Data Corporation of Park Ridge, N.J. in 1980, and references cited therein, all of which are incorporated herein by reference. More specifically, in the present invention the therapeutic agent or the vaccine is generally considered to be the synthetic construct or a polymer made therefrom. The product can, for example, be suspended in inert oil, suitably a vegetable oil such as sesame, peanut or olive oil. Alternatively, the product can be suspended in an aqueous isotonic buffer solution at a pH of about 5.6 to 7.4. Typically, such solutions will be made isotonic with sodium chloride and buffered with sodium citrate-citric acid or with phosphate. The solutions may be thickened with a thickening agent such as methylcellulose.

Vaccines may also be prepared in emulsified form, either water in oil or oil in water. Any of a wide variety of pharmaceutically acceptable emulsifying agents may be employed including, for example, acacia powder or an alkaryl polyether alcohol, sulfonate or sulfate such as Triton. Stabilizers such as sorbitol or hydrolyzed gelatin may also be added to any of the above-described compositions. The composition may also include an antibiotic such as neomycin or other anti-infective agent to prevent infection.

The vaccines of the invention may be defined as comprising a pharmaceutically acceptable carrier, of the general nature described above, together with an amount of a synthetic construct or polymer of the invention, which is sufficient to produce an immunological response. The amount that constitutes an effective amount may vary depending on whether the vaccine is intended as a first treatment or as a booster treatment and on the nature of the synthetic construct or polymer.

The antibodies of the invention may be used therapeutically. Antibodies with the proper biological properties can be useful directly as therapeutic agents. Furthermore, antibodies can be bound to a toxin to form an immunotoxin or to a radioactive material or drug to form a radiopharmaceutical or pharmaceutical. Methods for producing immunotoxins and radiopharmaceuticals of antibodies are well known (see, for example, *Cancer Treatment Reports* (1984) 68:317–328).

It may be convenient to provide the products of this invention in lyophilized or freeze dried powders ready to be reconstituted with a pharmaceutically acceptable carrier just prior to use. It is also within the purview of the present invention to use a vaccine or antibody described herein in conjunction with other therapeutic agents such as anti-inflamatories, antibiotics, and so forth.

As mentioned above, the present invention also includes antibodies produced in response to the synthetic constructs or polymers described above. The procedures for producing antibodies are described above. The antibodies, synthetic constructs and polymers of the invention may be employed in various diagnostic tests or assays such as immunoassays, precipitation assays, complement fixation assays, direct and indirect immunofluorescence assays, agglutination assays. Other assays that may be employed include agglutination assays, capillary precipitation assays, gel diffusion assays, and so forth. One or more of the products of the present invention may be labeled with a detectable label, or it may be caused to react with a labeled material complementary to the product of the invention.

For example, an immunoassay may be employed by the laboratory to analyze a sample for the presence and/or amount of an analyte, i.e., a component of interest or the substance to be determined. The analyte may be any chemical entity and includes ligands and receptors, where the ligand and the receptor are defined as members of a specific binding pair that have an affinity or avidity for each other. The ligand may be a hapten or antigen, where haptens generally range from about 100 to 5000 molecular weight and include drugs of abuse such as cocaine, marijuana, etc., and therapeutic drugs such as cyclosporin, theophylline, dilantia, antibiotics such as amikacin, tobramycin, anticonvulsants, etc., and the like.

An immunoassay may be homogeneous or heterogeneous. In the homogeneous assay approach the sample may be pretreated if necessary to remove unwanted materials. The reaction usually involves one member of a specific binding pair, e.g., a specific antibody, a labeled analyte and the sample analyte. The signal arising from the label is modified, directly or indirectly, upon the binding of the specific antibody to the labeled analyte. Both the binding of the specific binding pair members and the detection of the extent thereof are carried out in a homogeneous solution. Exemplary of the homogeneous assay are assays employing enzyme labels such as the EMITS assay described in U.S.

Pat. No. 3,817,837, the disclosure of which is incorporated herein by reference, the CEDIA assay, and so forth.

In the heterogeneous approach the reagents are usually the sample, a specific binding pair member such as an antibody, and means for producing a detectable signal. The sample is generally placed on a support, such as a microtiter plate or slide, and contacted with the specific binding pair member in an aqueous phase. The support is then separated from the liquid phase and either the support phase or the liquid phase is examined for a detectable signal employing means for producing such signal, which includes a label. Exemplary of heterogeneous assays are the radioimmunoassay (RIA), immunofluorescence methods, enzyme-linked immunoassays, such as the enzyme-linked immunosorbent assay (ELISA, see U.S. Pat. Nos. 3,654,090; 3,839,153; 3850,752; 4,016,043 and Re 29,169, the disclosures of which are incorporated herein by reference).

Enzyme immunoassays comprise quantitative procedures in which a specific binding reaction such as, in immunological cases, the antigen-antibody reaction, is monitored by enzyme activity measurements. The term ELISA is generally used for reagent excess assays of specific antibodies or antigens. However, sometimes, it is used interchangeably with EIA and immunoenzymometric assay. The various heterogeneous and homogeneous EIA's can be further characterized as either competitive or non-competitive (immunoenzymometric) assays. The characterization depends on whether the unlabeled antigen and the antigen linked to an enzyme or attached to a solid phase compete for a limited number of antibody binding sites, or whether the antigen or antibody to be measured is allowed to react alone with an excess of immune reactant. For a more detailed discussion of various enzyme assay techniques, see "Enzyme Immunoassay" by Edward T. Maggio, CRC Press, Inc., Boca Raton, Fla., 1980. See also, for example, U.S. Pat. Nos. 3,690,834; 3,791,932; 3,850,578; 3,853,987; 3,867, 517; 3,901,654; 3,935,074; 3,984,533; 3,996,345 and 4,098, 876, which listing is not intended to be exhaustive.

The assay components may be provided in the form of a kit where the components are in packaged combination in separate containers. One or more of the components may be combined in the same container where cross-reactivity is not a concern. The components may be in liquid or solid form. The kit usually contains all of the essential components necessary for carrying out an assay.

The sample to be analyzed for the presence of an analyte may be a body fluid or tissue including, for example, whole blood, blood fractions such as serum and plasma, synovial fluid, cerebro-spinal fluid, amniotic fluid, semen, cervical scrapings, cervical mucus, sputum, saliva, gingival fluid, urine, and the like. The amount of the sample used in the assay depends primarily on the amount of analyte in the sample and the nature of the sample. These considerations are well known in the art.

A particular embodiment of the present invention involves the use of the active site of human relaxin as epitopic sites of an antigen. Two tetrameric units are coupled by means of disulfides and injected into a rabbit for antibody production. Within two months antibody titers to relaxin of 1:10,000 to 1:20,000 are achieved. The antibodies obtained using the human sequence react as well with the porcine sequence and are expected to react with all relaxins that have an active site in common with that of the human sequence. As far as it is known, this represents the first time that a relaxin-recognizing antibody has been produced with a peptide rather than the intact relaxin.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope.

Example 1

Synthesis of an Antigen Support Unit (ASU) Containing the Receptor-binding Site of Human Relaxin The ASU backbone was synthesized on 4-methyl-benzhydrylamine resin (Matsueda, et al., *Peptides* (1981) 2:45–50) condensing first Boc-γ-aminobutyric acid followed by Boc-Lys(Fmoc)OH. The condensation was performed by standard Boc chemistry (Stewart, et al., Solid Phase Peptide Synthesis (1984) Pierce Chemical Company, Rockford, Ill.) on an ABI automatic peptide synthesizer (Perkin Elmer, Applied Biosystems, Model 430A). This sequence was repeated four times thereafter another Boc-⁻-aminobutyric acid was introduced followed by condensation of Boc-Cys (Acm) and final N terminal capping with acetic anhydride.

Example 2

The side chains of the four lysines were liberated by treatment with piperidine in dimethylformamide (1:4, v/v) and the peptide was introduced by stepwise condensation of N(α) Fmoc-protected amino acids in combination with trifluoroacetic acid labile side chain protecting groups using conventional Fmoc chemistry (Atherton, et al., (1989) Solid Phase Peptide Synthesis, A Practical Approach, IRL Press, Oxford). The N terminus was capped by treatment with acetic anhydride (10 equivalents, Stewart, et al., supra). The peptide linked to the side chain of each lysine was of the following sequence: Ac-Lys(Boc)-Leu-Ala-Gly-Arg(Pmc)-Glu(OBut)-Leu-Val-Arg(Pmc)-Ala-Gln-Ile-Ala-Ile-Ala-Gly-Asp(OBut) SEQ ID NO:1 where Pmc is 2,2,5,7,8-pentamethyl-chroman and OBut is tert-butoxy.

The peptide was dried and treated with trifluoroacetic acid/water (95:5 v/v) for 1 hour (h) at room temperature. The resin was filtered off, washed with trifluoroacetic acid and ether and dried. The peptide was liberated with HF/m-cresole (95:5 v/v) for 1 h at 0° C. The HF was evaporated and the peptide precipitated with ether and subsequently extracted with 50% acetic acid and lyophilized to give the product ASU. The peptide had the following sequence: Ac-KLAGRELVRAQIAIAGD (SEQ ID NO:4).

Example 3

Dimer Formation

The ASU's where dimerized by oxidative removal of the acetamidomethyl group. One micromole of ASU (8.9 mg) was dissolved in 2 mL of 50% acetic acid plus 20 μL 6 N HCl and 1 mL of 50 mM iodine in acetic acid was added. The reaction was stirred for 15 minutes at room temperature, excess iodine reduced with 1 M ascorbic acid in water and the linear ASU recovered by gel-filtration on Sephadex G25 sf (2.5 cm×40 cm, from Pharmacia, Upsala, Sweden) in 1 M acetic acid.

Example 4

Testing

The ASU of Example 3 was dissolved in complete Freund's adjuvant (50 μg/2 mL, from Sigma Chemical Company, St. Louis, Mo., U.S.A.) and 5 μg was injected subcutaneously into the loose skin over the haunches. Injections were repeated every four weeks using incomplete Freund's adjuvant. After four such injections the first blood samples were tested for antibody production. The treatment was continued for about four months, after which the rabbit produced a highly specific antibody against the receptor-binding site of relaxin.

The test for antibody production was as follows: All solutions were prepared in pH 7.5 buffer consisting of 50 mM sodium phosphate, 150 MM sodium chloride, 1% bovine serum albumin and 0.01% sodium azide. Synthetic human relaxin was radioiodinated in analogy to the procedure described for Relaxin-like Factor (RLF) (Bullesbach and Schwabe, *J. Biol. Chem.* (1995) 370:16011–16015) and native porcine relaxin was radioiodinated as described by Yang, et al., Endocrinology (1992) 130:179–185). The tracer was used at 20,000 to 30,000 cpm/100 μL for each assay. Serial diluted rabbit anti-serum was added (100 μL) and the assay medium was incubated for 12 hr at 4° C. To separate bound and free tracer, cellulose-bound goat-anti rabbit IgG was used. The reaction was shaken for 1 hr at room temperature and 3 mL of wash buffer (50 mM phosphate buffer, pH 7.4 containing 0.1% Tween 20) was added and the cellulose centrifuged off by low speed centrifugation (3000 rpm for 1-min). The supernatant was discarded and the pellet was washed 2 times with 3 mL of wash buffer. Thereafter, the pellet was counted in a gamma counter. High counts indicated binding of radioactive relaxin to rabbit IgG. The experiment allowed the determination of an optimal dilution of the serum. Under those conditions a standard RIA assay was performed in which increasing concentrations of porcine and/or human relaxin was used. Antibody binding was dose dependent and showed an ED50 of about 1 ng/mL for either porcine relaxin or human relaxin. Bombyxin II (a developmental factor of the silk moth with insulin-like structure showed no crossreactivity to this antibody).

Example 5

ASU with TCR Peptide(s)

The procedures of Examples 1–3 were followed with the exception that the following peptides, appropriately activated and protected, were substituted for the peptide of SEQ ID NO:1:

Vβ5.2(39–59)-ALGQGPQFIF QYYEEEERQR G (SEQ ID NO:2)

Vβ5.2(39–59)V-ALGQGPQFIF QTYEEEERQR G (SEQ ID NO:3)

In this way there are obtained the corresponding ASU's bearing TCR peptide side chains.

Example 6

Testing

The TCR peptide ASU's of Example 5 are used as test compounds in a suitably modified model of Experimental Autoimmune Encephalomyelitis (EAE) such as, for example, as described in U.S. Pat. No. 5,614,102. The model tests show a reduction in the severity and duration of symptoms of EAE.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A polymer comprising two or more synthetic constructs linked together wherein each of said synthetic constructs comprises a linear core chain having two or more side chains, each of said side chains pending directly from a different point on said linear core chain, each of said side chains comprising an epitopic site of an antigen selected from the group consisting of polypeptides and polysaccharides and combinations thereof, and wherein the epitopic sites of the side chains may be the same or different and wherein said linear core chain comprises at least one lysine-gamma aminobutyric acid dipeptide unit.

2. A support comprising the polymer of claim 1 coupled thereto.

3. A vaccine comprising the polymer of claim 1.

4. The polymer of claim 1 wherein the synthetic constructs are linked by disulfide bonds.

5. A polymer comprising two to four synthetic constructs linked together wherein each of said synthetic constructs comprises a linear sequence of amino acids having two or more peptides, each of said peptides pending directly from a different amino acid of said linear sequence, and wherein the peptides may be the same or different and wherein said linear sequence comprises at least one lysine-gamma aminobutyric acid dipeptide unit.

6. A support comprising the polymer of claim 5 coupled thereto.

7. A vaccine comprising the polymer of claim 5.

8. The polymer of claim 5 wherein the synthetic constructs are linked by disulfide bonds.

9. The polymer of claim 5 wherein said peptide has about 8 to 30 amino acids.

10. The polymer of claim 5 wherein said synthetic construct has a molecular weight greater than about 5,000.

11. The polymer of claim 5 wherein said side chains of said synthetic construct comprise at least 50% of the molecular weight of said synthetic construct.

12. The polymer of claim 5 wherein said amino acids other than said dipeptide are selected from the group consisting of thiopropionic acid, lysine, gamma aminobutyric acid and cysteine.

13. A polymer comprising a synthetic construct of the formula:

14. The polymer of claim 13 wherein said Antigen is an epitopic site of human relaxin.

15. A polymer comprising a synthetic construct of the formula:

16. The polymer of claim 15 wherein Antigen-1 and Antigen-2 are different epitopic sites of human relaxin.

17. A polymer comprising two or more synthetic constructs linked together wherein each of said synthetic constructs is a linear chain that has the formula:

wherein W is Ac-KLAGRELVRAQIAIAGD-(SEQ ID NO:4), Ac is acetyl, Cys is cysteine, GABA is gamma-aminobutyric acid, and Lys is lysine and wherein W is attached to Lys through D.

* * * * *

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Lys(Boc)
<220> FEATURE:
<221> NAME/KEY: MOD_RES
<222> LOCATION: (5)
<223> OTHER INFORMATION: Arg(Pmc)
<220> FEATURE:
<221> NAME/KEY: MOD_RES
<222> LOCATION: (6)
<223> OTHER INFORMATION: Glu(OBut)
<220> FEATURE:
<221> NAME/KEY: MOD_RES
<222> LOCATION: (9)
<223> OTHER INFORMATION: Arg(Pmc)
<220> FEATURE:
<221> NAME/KEY: MOD_RES
<222> LOCATION: (17)
<223> OTHER INFORMATION: Asp(OBut)

<400> SEQUENCE: 1

Lys Leu Ala Gly Arg Glu Leu Val Arg Ala Gln Ile Ala Ile Ala Gly
 1               5                  10                  15
```

Asp

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Leu Gly Gln Gly Pro Gln Phe Ile Phe Gln Tyr Tyr Glu Glu Glu
 1               5                  10                  15

Glu Arg Gln Arg Gly
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Gly Gln Gly Pro Gln Phe Ile Phe Gln Thr Tyr Glu Glu Glu
 1               5                  10                  15

Glu Arg Gln Arg Gly
            20

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Lys

<400> SEQUENCE: 4

Lys Leu Ala Gly Arg Glu Leu Val Arg Ala Gln Ile Ala Ile Ala Gly
 1               5                  10                  15

Asp

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ser Leu Leu Val Asp Val
 1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)
<223> OTHER INFORMATION: Ac-Cys, Acm protected
<220> FEATURE:
<221> NAME/KEY: MOD_RES
<222> LOCATION: (2)
<223> OTHER INFORMATION: gamma-aminobutyric acid
<220> FEATURE:
<221> NAME/KEY: MOD_RES
<222> LOCATION: (4)
<223> OTHER INFORMATION: gamma-aminobutyric acid
<220> FEATURE:
<221> NAME/KEY: MOD_RES
<222> LOCATION: (6)
<223> OTHER INFORMATION: gamma-aminobutyric acid
<220> FEATURE:
<221> NAME/KEY: MOD_RES
<222> LOCATION: (8)
<223> OTHER INFORMATION: gamma-aminobutyric acid
<220> FEATURE:
<221> NAME/KEY: MOD_RES
<222> LOCATION: (10)
<223> OTHER INFORMATION: gamma-aminobutyric acid
<220> FEATURE:
<221> NAME/KEY: MOD_RES
<222> LOCATION: (12)
<223> OTHER INFORMATION: gamma-aminobutyric acid
<220> FEATURE:
<223> OTHER INFORMATION: see specification as filed for detailed
      description of protected residues and preferred embodiments

<400> SEQUENCE: 6

Cys Xaa Lys Xaa Lys Xaa Lys Xaa Lys Xaa Lys Xaa
 1               5                  10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ile Val Asp Glu Ala Ala Leu
 1               5
```